United States Patent
Zhao et al.

(10) Patent No.: US 8,311,310 B2
(45) Date of Patent: Nov. 13, 2012

(54) METHODS AND APPARATUS TO INTEGRATE SYSTEMATIC DATA SCALING INTO GENETIC ALGORITHM-BASED FEATURE SUBSET SELECTION

(75) Inventors: Luyin Zhao, Belleville, NY (US); Lilla Boroczky, Mount Kisco, NY (US); Kwok Pun Lee, Ossining, NY (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 620 days.

(21) Appl. No.: 12/377,245

(22) PCT Filed: Aug. 2, 2007

(86) PCT No.: PCT/IB2007/053048
§ 371 (c)(1),
(2), (4) Date: Feb. 11, 2009

(87) PCT Pub. No.: WO2008/017991
PCT Pub. Date: Feb. 14, 2008

(65) Prior Publication Data
US 2010/0177943 A1 Jul. 15, 2010

Related U.S. Application Data

(60) Provisional application No. 60/822,098, filed on Aug. 11, 2006.

(51) Int. Cl.
*G06K 9/00* (2006.01)
(52) U.S. Cl. ......... 382/133; 382/128
(58) Field of Classification Search .......... 382/128–134, 382/159–161, 155–156
See application file for complete search history.

(56) References Cited

U.S. PATENT DOCUMENTS

| | | | |
|---|---|---|---|
| 5,987,094 A | 11/1999 | Clarke et al. | |
| 6,470,092 B1 | 10/2002 | Li et al. | |
| 7,840,062 B2* | 11/2010 | Boroczky et al. | 382/159 |
| 2002/0165837 A1 | 11/2002 | Zhang et al. | |
| 2004/0122787 A1* | 6/2004 | Avinash et al. | 706/50 |
| 2004/0252870 A1* | 12/2004 | Reeves et al. | 382/128 |

(Continued)

FOREIGN PATENT DOCUMENTS

WO 2005078629 A2 8/2005

(Continued)

OTHER PUBLICATIONS

Boroczky, L.; Zhao, L.; Lee, K.P.; , "Feature subset selection for improving the performance of false positive reduction in lung nodule CAD," Computer-Based Medical Systems, 2005. Proceedings. 18th IEEE Symposium on , vol., no., pp. 85-90, Jun. 23-24, 2005;doi: 10.1109/CBMS.2005.53;URL: http://ieeexplore.ieee.org/stamp/stamp.jsp?tp=&arnumber=146767.*

(Continued)

*Primary Examiner* — Tony Ko
*Assistant Examiner* — Jori S Reilly-Diakun (57) ABSTRACT

Methods and apparatus for training a system for developing a process of data mining, false positive reduction, computer-aided detection, computer-aided diagnosis and artificial intelligence are provided. A method includes choosing a training set from a set of training cases using systematic data scaling and creating a classifier based on the training set using a classification method. The classifier yields fewer false positives. The method is suitable for use with a variety of data mining techniques including support vector machines, neural networks and decision trees.

17 Claims, 10 Drawing Sheets

U.S. PATENT DOCUMENTS

| | | | | |
|---|---|---|---|---|
| 2009/0175514 A1* | 7/2009 | Zhao et al. | ................... | 382/128 |
| 2009/0175531 A1* | 7/2009 | Boroczky et al. | ............. | 382/159 |

FOREIGN PATENT DOCUMENTS

| | | |
|---|---|---|
| WO | 2006054269 A2 | 5/2006 |

OTHER PUBLICATIONS

Boroczky, L.; Luyin Zhao; Lee, K.P.; , "Feature Subset Selection for Improving the Performance of False Positive Reduction in Lung Nodule CAD," Information Technology in Biomedicine, IEEE Transactions on , vol. 10, No. 3, pp. 504-511, Jul. 2006;doi: 10.1109/TITB.2006.872063;URL: http://ieeexplore.ieee.org/stamp/stamp.jsp?tp=&arnumber=1650504&isnumber=.*

Batista, G.; Prati, R.; Monard, M.; "A study of the behavior of several methods for balancing machine learning training data", Sigkdd Explorations, 2004, vol. 6, Issue 1, pp. 20-29; http://dl.acm.org/citation.cfm?id=1007735.*

Kohavi et al, The Wrapper Approach, Artifical Intelligence, 1997, pp. 273-324.

Suzuki et al, "Massive Training Artifical Neural Network (MTANN) for Reduction of False Positives in Computerized Detection of Lung Nodules in Low-Dose Computed Tomography", 30 Med. Physics, 2003, pp. 1602-1617.

Mousa et al, "Lung Nodule Classification Utilizing Support Vector Machines", Int'l Conf. on Image Processing, Summary, 2002, 1 page.

Suzuki et al, "Effect of a Small Number of Training Cases on the Performance of Massive Training Artificial Neural Network (MTANN) for Reduction of False Positives in Computerized Detection of Lung Nodules in Low-Does CT", Medical Imaging, vol. 5032, 2003, pp. 1355-1366.

Batista et al, "A Study of the Behavior of Several Methods for Balancing Machine Learning Training Data", 6 SIGKDD Explorations 20, 2004, pp. 20-29.

Ge et al, "Computer-Aided Detection of Lung Nodules: False Positive Reduction Using A 3D Gradient Field Method and 3D Ellipsoid Fitting", Medical Imaging, 2004, pp. 2443-2454.

Eshelman, "The CHC Adaptive Search Algorithm: How to Have Safe Search When Engaging in Nontraditional Genetic Recombination", Foundations of Genetic Algorithms, 1991, pp. 265-283.

Schaffer et al, "A Genetic Algorithm Approach for Discovering Diagnostic Patterns in Molecular Measurement Data", Proceedings of the 2005 IEEE Symposium on Computational Intelligence in Bioinformatics and Computational Biology, 2005, 8 Pages.

Boser et al, "A Training Algorithm for Optimal Margin Classifiers", Presented at 5TH Annual ACM Workshop on Computational Learning Theory, 1992, 9 Pages.

* cited by examiner

METHODS AND APPARATUS TO INTEGRATE SYSTEMATIC DATA SCALING INTO GENETIC ALGORITHM-BASED FEATURE SUBSET SELECTION

The technical field of the application is methods and apparatus for integrating systematic data scaling into genetic algorithm-based feature subset selection systems for data mining, false positive reduction (FPR), computer-aided detection (CAD), computer-aided diagnosis (CADx) and artificial intelligence.

CAD algorithms have been developed to automatically identify medically important anatomical features, such as suspicious lesions from multi-slice computed tomography (MSCT) scans, and thereby provide a second opinion for use by a radiologist. These algorithms aid in the early detection of cancers, leading to increased survival rates. For example, lung cancer is one of the most common fatal diseases, with 162,460 deaths due to lung cancer expected in 2006 in the United States (American Cancer Society, "Cancer Facts & Figures 2006," Atlanta 2006), and a 5-year survival rate for lung cancer patients of only about 15% despite improvements in surgical techniques and therapies. However, the survival rate improves significantly to about 50% for cases detected when the disease is still localized. Thus, early detection and diagnosis of suspicious lesions allows for early intervention and can lead to better prognoses and survival rates.

Use of machine learning techniques as a post-processing step is known to eliminate false positive structures that are misidentified as lung nodules by a CAD algorithm. Mousa and Khan used support vector machines (SVM) to classify lung nodules from non-nodules (W. A. H. Mousa & M. A. U. Khan, *Lung nodule classification utilizing support vector machines*, presented at Int'l Conf. On Image Processing, 2002).

Ge et al. have proposed a linear discriminant classifier based on 3β features (Ge et al., *Computer aided detection of lung nodules: false positive reduction using a 3D gradient field method*, presented at Medical Imaging 2004: Image Processing, San Diego 2004).

Suzuki et al. have proposed a massive training artificial neural network (MTANN) which is capable of operating on image data directly and does not require feature extraction (K. Suzuki et al., *Massive training artificial neural network (MTANN) for reduction of false positives in computerized detection of lung nodules in low-dose computed tomography*, 30 MED. PHYSICS 1602-17, 2003). They concluded that a combination of MTANN and a rule-based/linear-discriminant classifier rather than MTANN alone might be useful for FPR. Most existing work on FPR follows the same methodology for supervised learning: starting with a collection of data with ground truth, a classifier is trained with the data using a set of features (computed from the images) that one or more users deem to be appropriate.

While recent advances in MSCT enable the detection of a cancer such as lung, liver or breast cancer at an earlier stage than before, these methods also result in a huge amount of data that must be interpreted by a radiologist, a costly and time consuming procedure. CAD algorithms have high sensitivity, however, none of them operate with perfect accuracy (i.e. able to detect all and only structures that are true lung nodules). Some non-nodule structures (e.g. blood vessels) are often labeled erroneously as nodules. Since a clinician such as a radiologist has to examine each identified structure, it is highly desirable to eliminate as many false positives (FP) as possible while retaining the true positives (TP), i.e., nodules, in order to avoid fatigue and mistakes caused by unnecessary examinations on false positives. This is known as false positive reduction (FPR). Unlike other classification tasks that aim to reduce the total number of misclassified cases, the objective here is to eliminate as many FPs as possible (maximizing specificity) under the constraint that all TPs be retained (maintaining 100% sensitivity).

Although false positive reduction systems have been described, the goal of such systems, which is maximum specificity while maintaining 100% sensitivity, remains elusive.

An embodiment of the invention provides a method of improving classification accuracy and reducing false positives in data mining, computer-aided detection, computer-aided diagnosis and artificial intelligence. The method includes choosing a training set from a set of training cases using systematic data scaling. The method also includes creating a classifier based on the training set using a classification method, wherein the systematic data scaling method and the classification method produce the classifier thereby reducing false positives and improving classification accuracy.

In a related embodiment, the classifier is selected from the group consisting of support vector machines, neural networks, and decision trees.

Another embodiment further involves evaluating the classifier produced by the classification method based on the training set using a testing set.

In another embodiment, choosing training set further involves removing from the training set false nodules that form Tomek links with true nodules until a threshold is met. In a related embodiment the threshold is determined with respect to a downscaling factor, x, such that the number of false nodules remaining in the training set after systematic data scaling is no more than x times the number of true nodules in the training set.

In a related embodiment, the method includes validating the classifier with the set of testing cases or a subset thereof.

Also provided is a genetic algorithm that when executed implements any of the above methods. In a related embodiment, the genetic algorithm is the CHC algorithm (L. J. Eshelman, *The CHC Adaptive Search Algorithm: How to Have Safe Search When Engaging in Nontraditional Genetic Recombination*, in FOUNDATIONS OF GENETIC ALGORMIMS 265-83, G. J. E. Rawlines, ed. 1991).

Also provided is a method of choosing features from a feature pool using the abovementioned genetic algorithm, the method having the steps of: providing each of a first genetic algorithm and a second genetic algorithm according to the above methods, wherein the first genetic algorithm is used to determine the best size of the feature set; and, fixing the feature set size and using the second genetic algorithm to select the features. In a related embodiment, in providing the first genetic algorithm, the method further comprises analyzing results using at least one of: number of occurrences of chromosomes representing different feature subset sizes and number of average errors. In a further embodiment, "number of average errors" is a number of misclassified lung nodules resulted by the classifier based on these chromosomes.

Also provided is a computer-readable medium which when executed implements any of the above methods.

Also provided is an article of manufacture, which is an imaging device or a false positive reduction device, wherein the device is a computer that is programmed to analyze image data by implementing any of the above methods.

In a related embodiment, in the article of manufacture above, the imaging device is selected from the group consisting of: computed tomography (CT), computed axial tomography (CAT), multi-slice computed tomography (MSCT), body section roentgenography, ultrasound, magnetic resonance imaging (MRI), magnetic resonance tomography (MRT), nuclear magnetic resonance (NMR), X-ray, microscopy, fluoroscopy, tomography, and digital imaging. In a further embodiment of the article of manufacture above, the article is a lung nodule CAD system.

Accordingly, it is an object of the present invention to integrate systematic data scaling into the evaluation of candidate feature subsets in a genetic algorithm.

Support Vector Machines (SVMs) are a relatively new tool for machine learning (B. E. Boser, I. Guyon & V. Vapnik, *A training algorithm for optimal margin classifiers*, presented at 5$^{th}$ Annual ACM Workshop on Computational Learning Theory, Pittsburgh 1992). SVMs have gained increasing popularity since the late 1990s (V. N. VAPNIK, THE NATURE OF STATISTICAL LEARNING THEORY (1995); V. N. VAPNIK, STATISTICAL LEARNING THEORY, 1998). Support Vector Machines are currently among the best performers for a number of classification tasks ranging from text to genomic data, however, a number of problems remain, as described herein.

SVM handles the task of classifying objects into one of two classes and supposes that some examples have already been classified. The goal in this type of supervised machine learning is to come up with a function that "correctly" classifies any new object. SVM theory can be formalized as follows: for a set $\{x_i, y_i\}$ of size m of training data, each data point described by a feature vector $x_i \in R^d$ and a priori knowledge that each $x_i$ belongs to one of two classes $y_i \in \{-1,1\}$ (i=1, ..., m). Given a new data point x, the goal of SVM theory is to determine a function $f$ such that $\{x, f(x)\}$ is in some sense similar to the given training data. Suppose it is possible to find a hyperplane $w \cdot x + b = 0$ (where the dot denotes inner product) such that all the positive examples (y=1) lie on one side of the plane and the negative examples (y=−1) lie on the other side, i.e.

$$w \cdot x_i + b \geq +1 \text{ if } y_i = 1$$

$$w \cdot x_i + b \leq -1 \text{ if } y_i = -1$$

In this case, the training set is linearly separable. Given a new data point x, $w \cdot x + b$ is computed and the sign of the value tells whether x is a positive or negative example. In other words, the function $f(x) = \text{sgn}(w \cdot x + b)$ determines the classification of any new vector x.

In most circumstances, it is not be possible to find a hyperplane that will neatly separate the positive and negative examples. SVM maps the original feature vectors to a (usually) higher dimensional space where such a hyperplane can be found:

$$\Phi : x \rightarrow \phi(x)$$

This mapping $\Phi$ is called a kernel function. There are many hyperplanes that can separate the data set. A hyperplane is selected such that the minimum distance of the training data vectors (i.e., the perpendicular distance to the hyperplane) is maximal. Vectors at this minimum distance from the hyperplane are called support vectors. The set of support vectors determines the separating hyperplane. The other vectors can be discarded without changing the solution, and if any of the support vectors are removed, the hyperplane will change. Finding this hyperplane is thus an optimization problem.

On the surface, mapping into a higher dimensional space can cause computational problems. However, SVM theory shows that one can choose kernel functions such that the resulting function $f$ is computationally attractive.

The word "classifier" as used herein describes any type of method or apparatus capable of predicting to what group or category an object belongs. This definition includes, but is not limited to, data mining tools and techniques such as Support Vector Machines, neural networks and decision trees.

The term "classification method" as used herein describes any means of producing a classifier. This definition includes, but is not limited to, data mining tools and techniques such as the algorithm of Boser et al. for creating SVMs, C4.5, J4.8, and the APRIORI method (B. E. Boser, I. Guyon & V. Vapnik, *A training algorithm for optimal margin classifiers*, presented at 5$^{th}$ Annual ACM Workshop on Computational Learning Theory, Pittsburgh 1992).

An embodiment of the invention provided herein is a machine-learning-based FPR unit having three major processing components: feature extraction, SVM driven GA-based feature subset selection and an SVM classifier. The feature extraction unit computes several 2β and 3β features from CT scans for use in discriminating between true nodules and non-nodules. These features constitute the feature pool for the feature subset selection step, which is carried out only in the design phase of the system. Once an optimal feature subset has been selected and a classifier constructed from it, the system consists of only feature extraction and a classifier. An embodiment of the invention uses a Support Vector Machine because of its superior performance for various classification tasks including medical decision support. Other classifiers such as neural networks can also be used.

To prevent unnecessary computations and over-fitting, and to ensure a reliable classifier, a feature subset is selected using Genetic Algorithms (GAs). The wrapper approach involves a feature selection algorithm coupled with a classifier to produce the selection criteria (R. Kohavi & G. H. John, *The Wrapper Approach*, 97 ARTIFICIAL INTELLIGENCE 273-324, 1997). One possible classifier/feature selection algorithm combination is an SVM and a GA called CHC is used (L. J. Eshelman, *The CHC Adaptive Search Algorithm How to Have Safe Search When Engaging in Nontraditional Genetic Recombination*, in FOUNDATIONS OF GENETIC ALGORITHMS 265-83, G. J. E. Rawlines, ed. 1991). CHC is desirable because of its robust search behavior for a large class of problems. The feature selection method is able to automatically determine the optimal size and the set of such features.

In general, the method herein includes creating a number of "chromosomes" that consist of multiple "genes" with each gene representing a selected feature (D. Schaffer et al., *A Genetic Algorithm Approach for Discovering Diagnostic Patterns in Molecular Measurement Data*, PROCEEDINGS OF THE 2005 IEEE SYMPOSIUM ON COMPUTATIONAL INTELLIGENCE IN BIOINFORMATICS AND COMPUTATIONAL BIOLOGY 1, 2005).

The set of features represented by a chromosome is used to train an SVM using the portion of training data corresponding to the feature subset. The fitness of the chromosome is evaluated according to how well the resulting SVM performs on testing data. In one embodiment, a hierarchical fitness function based on the true nodule retention and false positive elimination rates of the SVM classification is carried out on the testing set. In alternative embodiments, it is possible to develop and use different fitness functions.

At the start of this process a population of chromosomes is generated by randomly choosing features to form chromosomes. The algorithm then iteratively searches for those chromosomes that have higher performance values (higher fitness). At each generation the GA evaluates the fitness of each chromosome in the population and, through two main evolutionary methods, mutation and crossover, creates new chromosomes from the fitter ones. Genes that are within good chromosomes are more likely to be retained for the next generation and those with poor performance are more likely to be discarded. Eventually a collection of features with high performance is found through this process of survival of the fittest.

It is an object of the invention to improve the performance of a genetic algorithm by integrating systematic data scaling into the evaluation of candidate feature subsets. In this embodiment, systematic data scaling is used to choose a training set from a set of training cases.

For each set of candidate feature subset, a training set is selected from the set of training cases. Borderline false positive cases are removed from the training set. The training set is then used to produce a classifier that is used to evaluate the candidate feature subset's fitness as part of the genetic algorithm.

Figure 1:
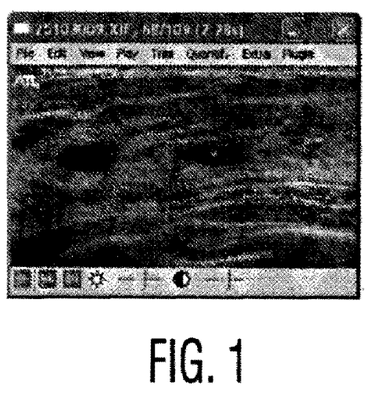
FIG. 1 is an image of a CAD output of a breast ultrasound scan with one lesion detected and delineated.
Figure 2:
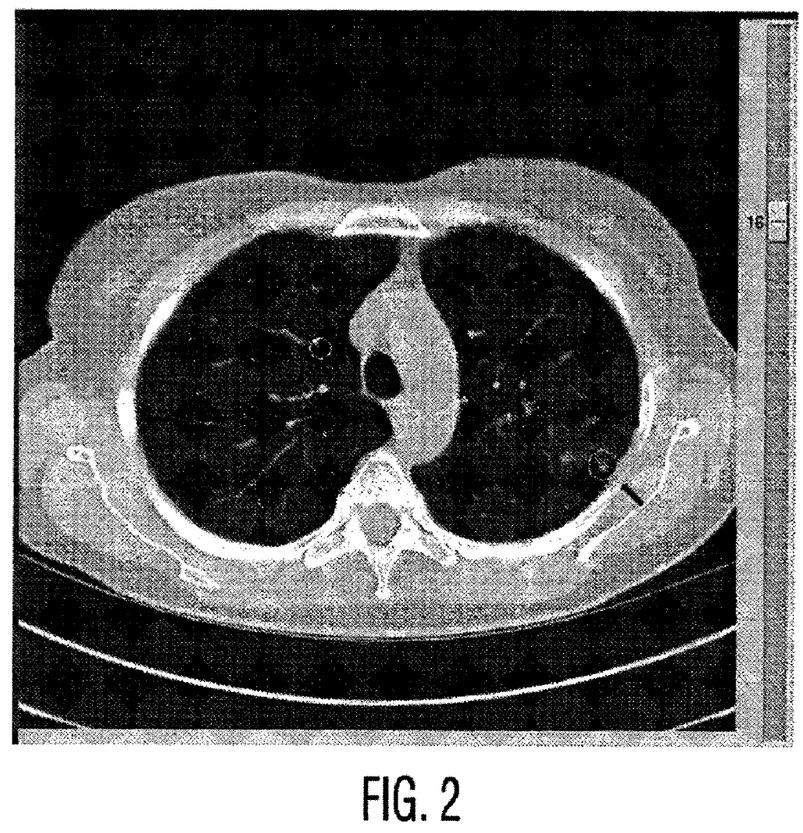
FIG. 2 is a CAD output of a lung CT scan with a two detected lesions identified.
Figure 3:
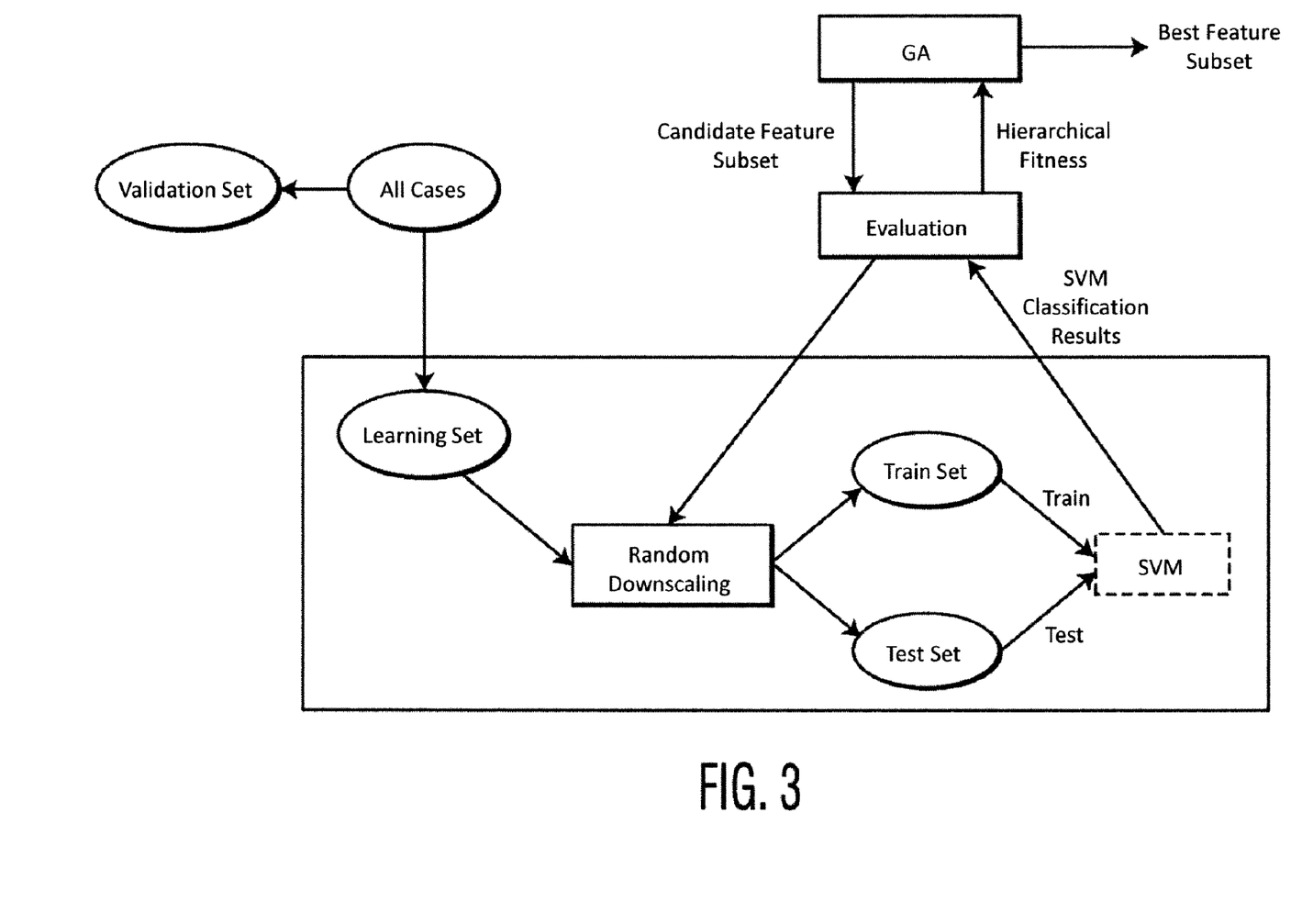
FIG. 3 is a diagram of a genetic algorithm based feature subset selection.
Figure 4:
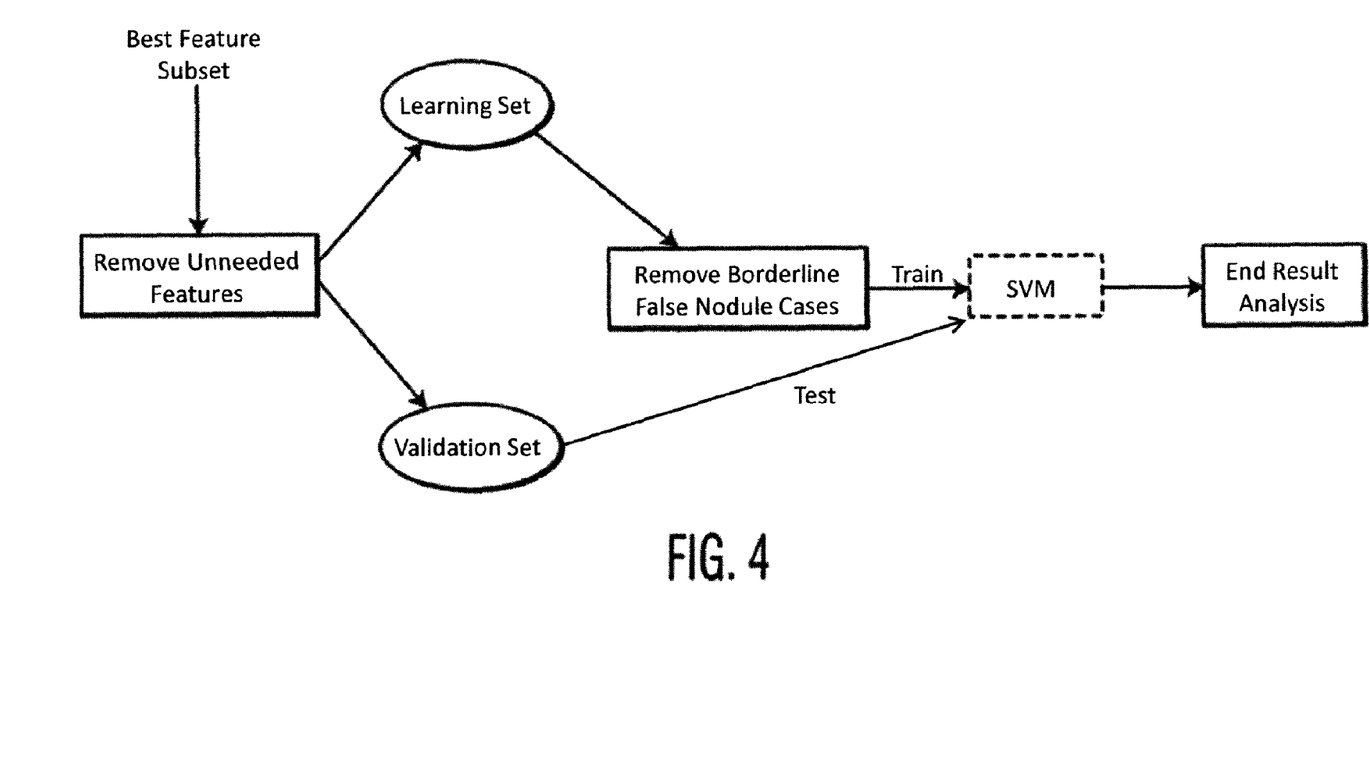
FIG. 4 is a diagram of a false positive reduction process using the best feature subset selected using the best feature subset selected in FIG. 3.
Figure 5:
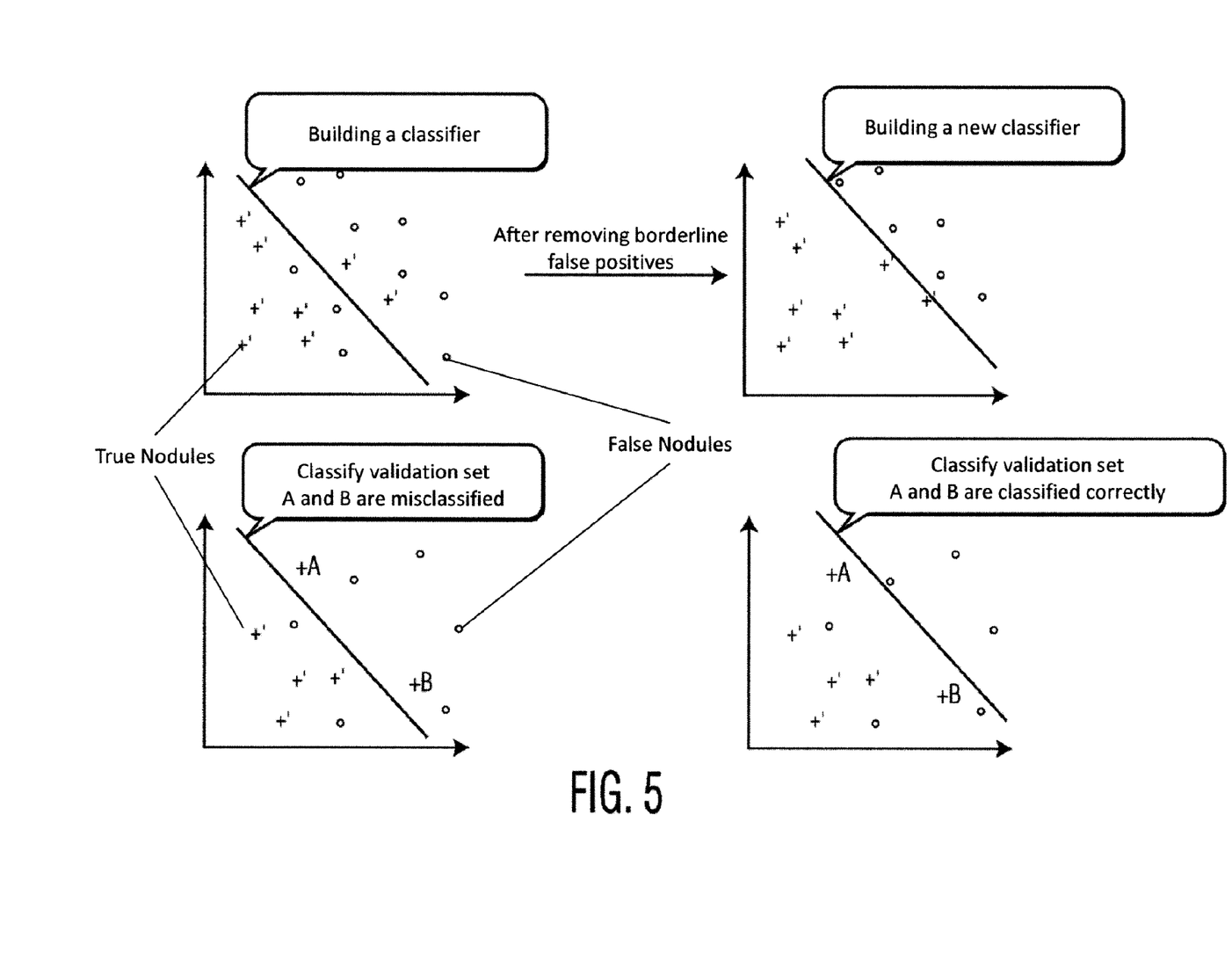
FIG. 5 shows the effect of operation of the systematic downscaling method to remove false positives from the train set.
Figure 6:
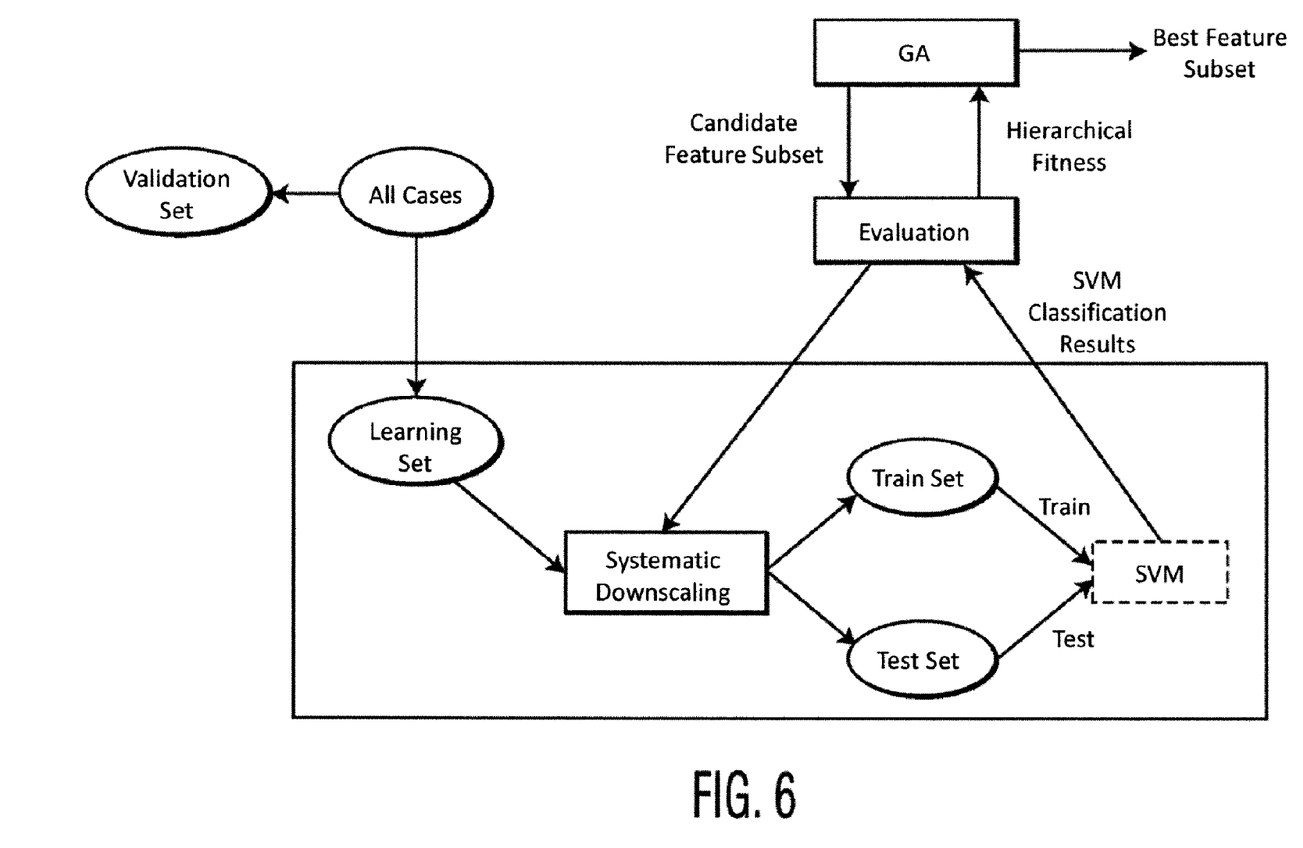
FIG. 6 is a diagram depicting the integration of systematic data scaling (systematic downscaling) into the GA feature subset selection process.
Figure 7:
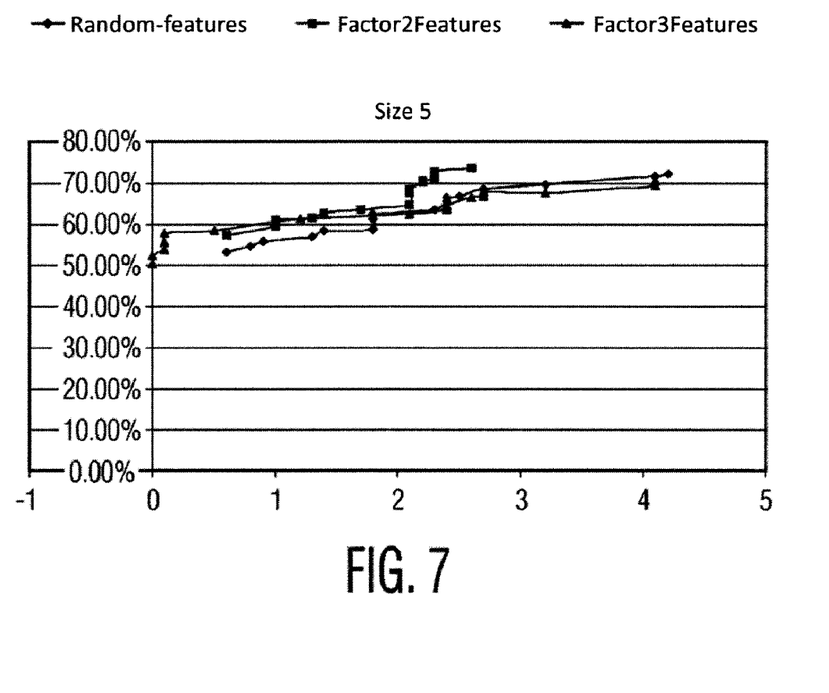
FIG. 7 is a graph showing the performance of genetic algorithms incorporating random downscaling, systematic data scaling (downscaling factor of 2) and systematic data scaling (downscaling factor of 3) for feature subsets of size 5.
Figure 8:
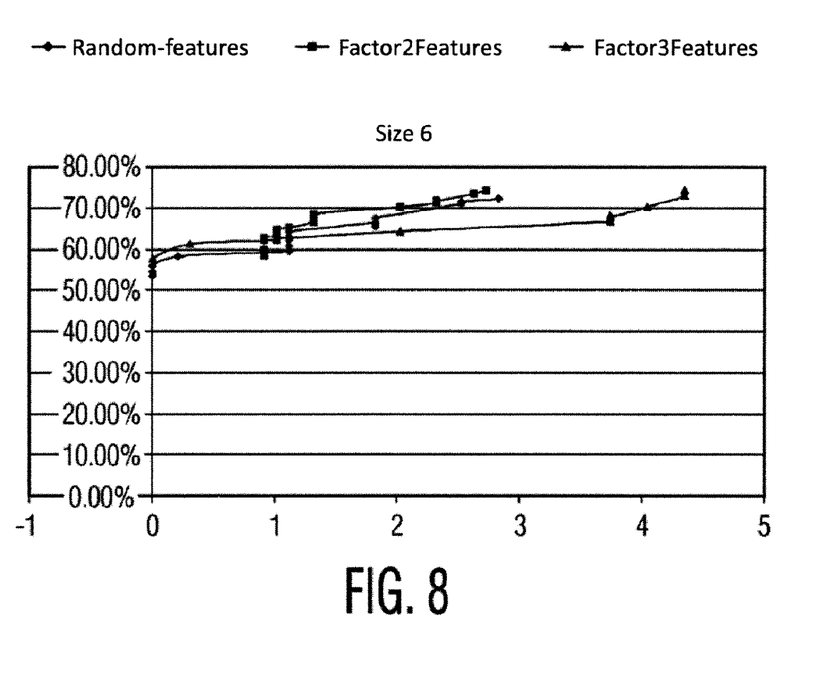
FIG. 8 is a graph showing the performance of genetic algorithms incorporating random downscaling, systematic data scaling (downscaling factor of 2) and systematic data scaling (downscaling factor of 3) for feature subsets of size 6.
Figure 9:
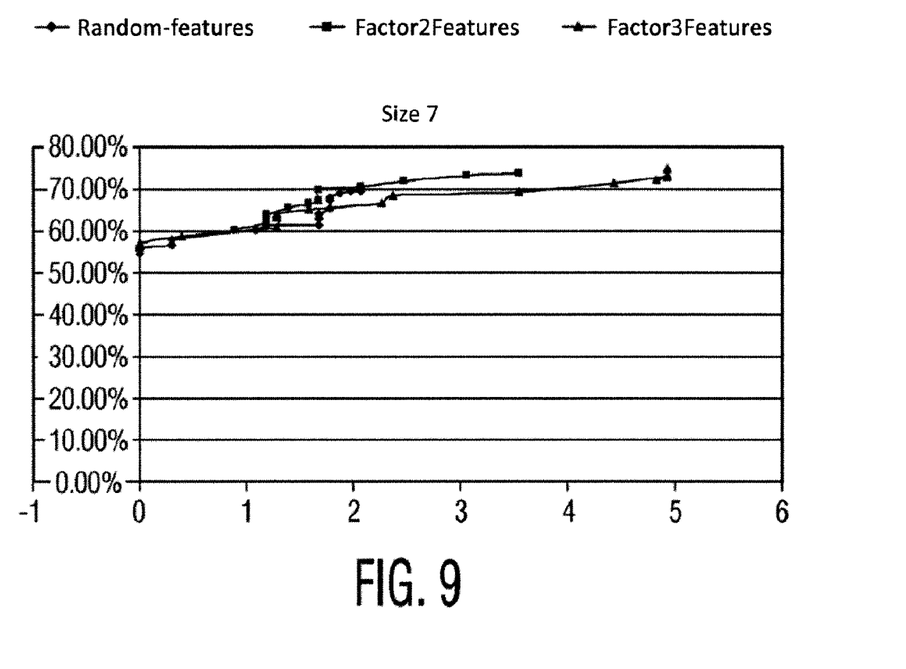
FIG. 9 is a graph showing the performance of genetic algorithms incorporating random downscaling, systematic data scaling (downscaling factor of 2) and systematic data scaling (downscaling factor of 3) for feature subsets of size 7.
Figure 10:
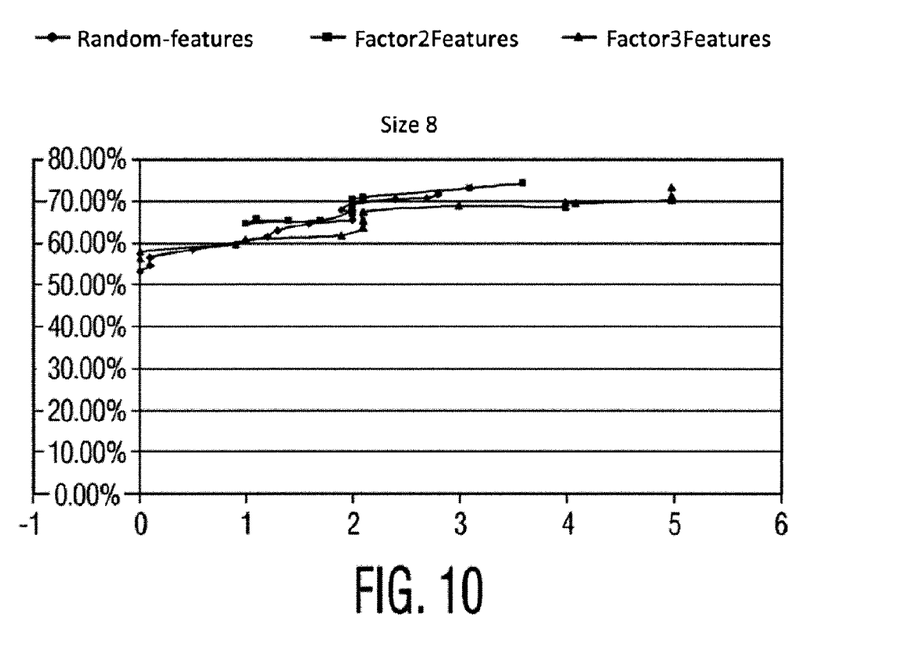
FIG. 10 is a graph showing the performance of genetic algorithms incorporating random downscaling, systematic data scaling (downscaling factor of 2) and systematic data scaling (downscaling factor of 3) for feature subsets of size 8.
Figure 11:
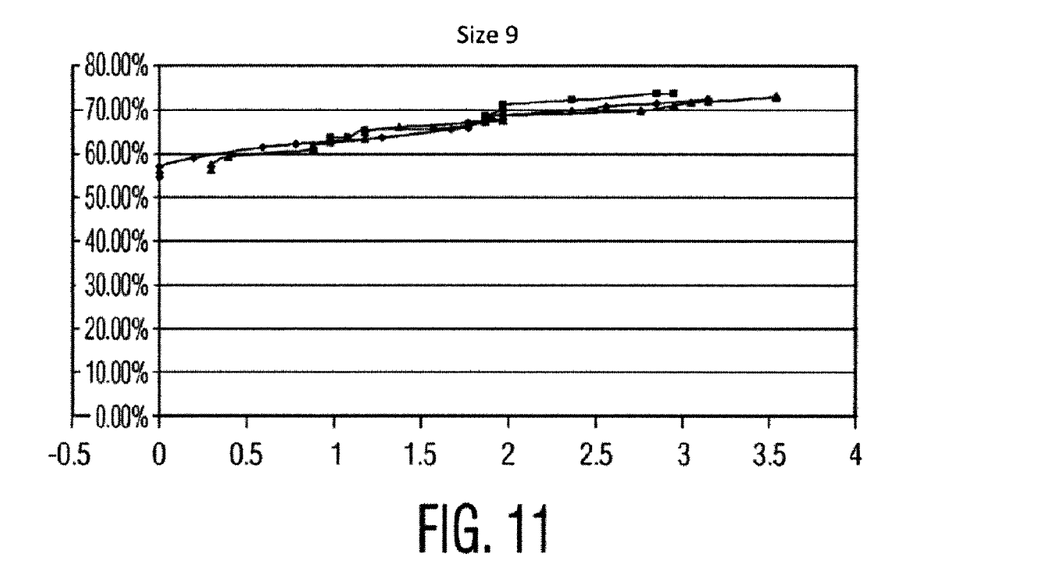
FIG. 11 is a graph showing the performance of genetic algorithms incorporating random downscaling, systematic data scaling (downscaling factor of 2) and systematic data scaling (downscaling factor of 3) for feature subsets of size 9.
Figure 12:
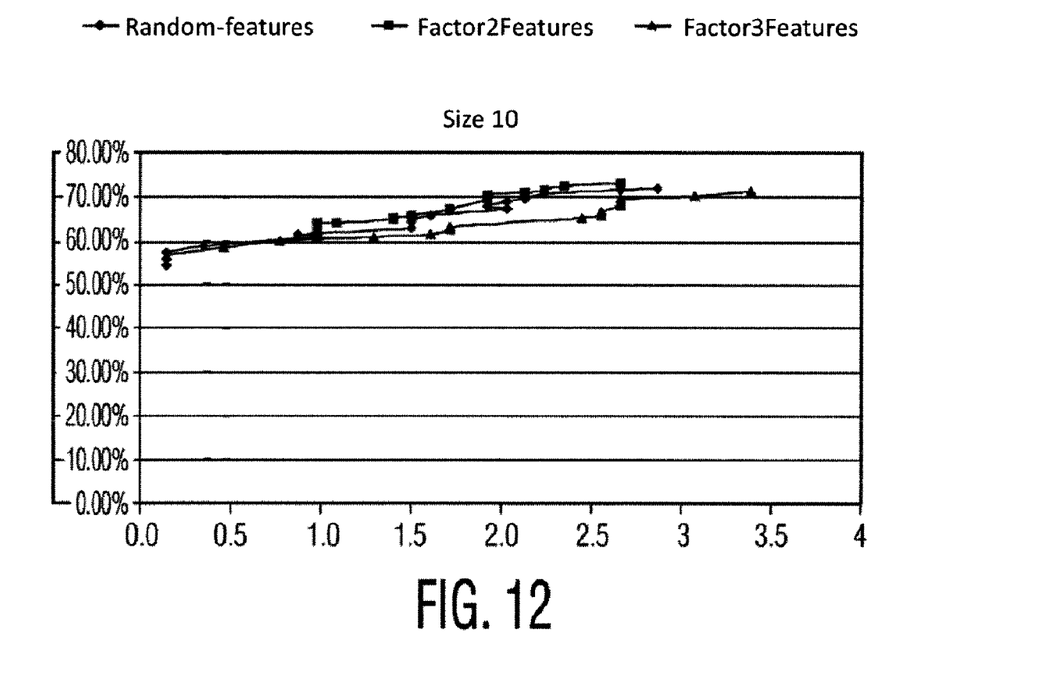
FIG. 12 is a graph showing the performance of genetic algorithms incorporating random downscaling, systematic data scaling (downscaling factor of 2) and systematic data scaling (downscaling factor of 3) for feature subsets of size 10.
Figure 13:
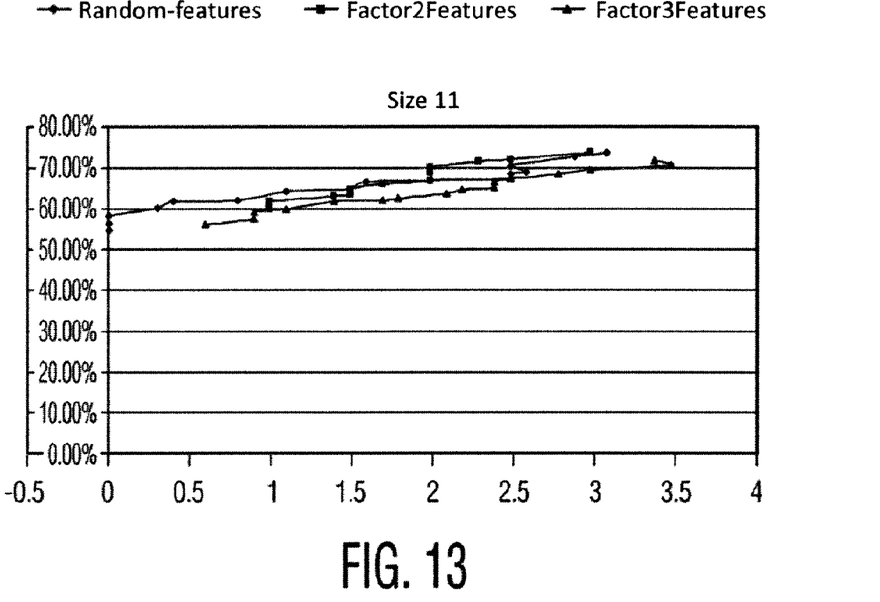
FIG. 13 is a graph showing the performance of genetic algorithms incorporating random downscaling, systematic data scaling (downscaling factor of 2) and systematic data scaling (downscaling factor of 3) for feature subsets of size 11.
Figure 14:
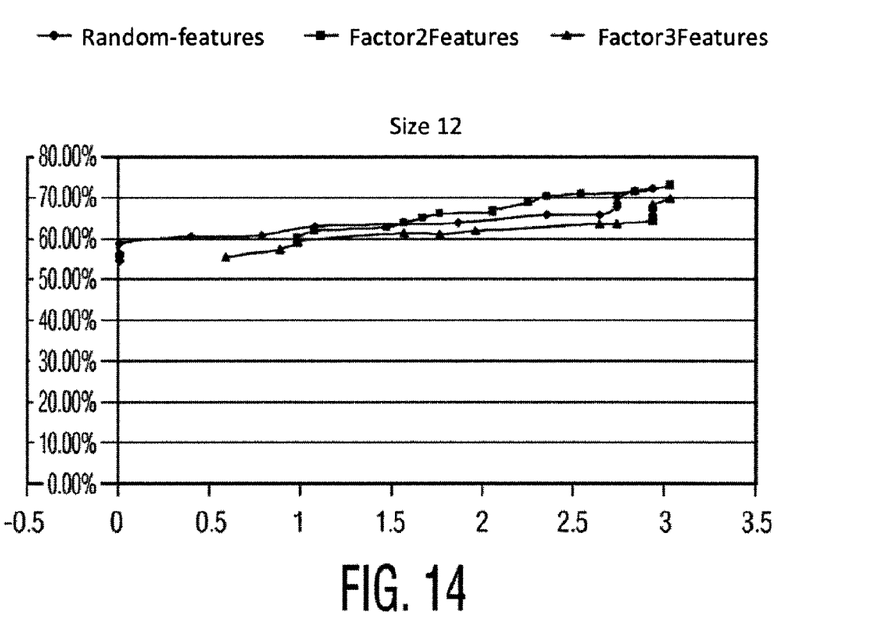
FIG. 14 is a graph showing the performance of genetic algorithms incorporating random downscaling, systematic data scaling (downscaling factor of 2) and systematic data scaling (downscaling factor of 3) for feature subsets of size 12.
Figure 15:
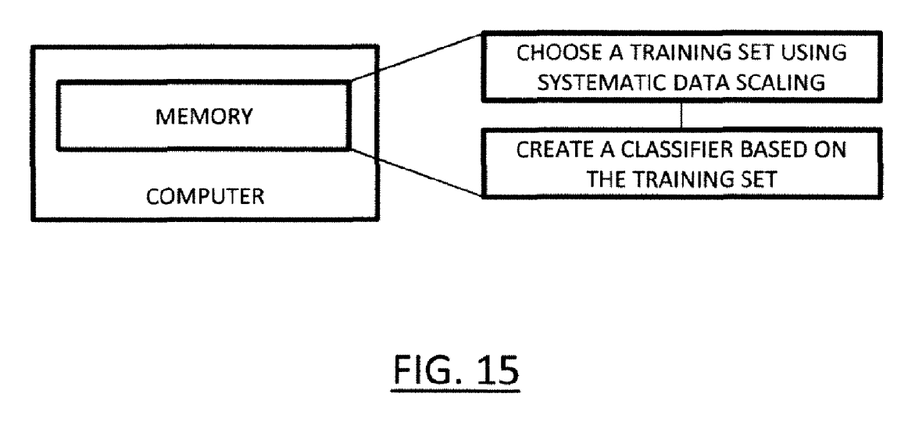
FIG. 15 is a diagram of a computer implementing a method of improving classification accuracy and reducing false positives in data mining, computer-aided detection, computer-aided diagnosis and artificial intelligence.

In another embodiment, the borderline false positives can be identified through the concept of Tomek links (G. E. A. P. A. Batista, *A Study of the Behavior of Several Methods for Balancing Machine Learning Training Data*, 6 SIGKDD EXPLORATIONS 20-29, 2004). Given a true nodule case A and a false nodule case B, let d(A,B) be the distance between A and B. An (A, B) pair is called a Tomek link if there is not an example C (which can be either a true nodule or a false nodule) such that $d(A,C)<d(A,B)$ or $d(B,C)<d(A,B)$. If A and B form a Tomek link, then either A or B is noise or both A and B are borderline. When Tomek links are used in this false positive reduction scenario, only the false positive case B is removed as a downscaling method. FIG. 5 shows how this downscaling method works to retain more of the true nodules.

In a further embodiment, the number of false positive cases removed can be adjusted to better attain desired specificity or sensitivity. This is accomplished through the use of a downscaling factor x. The downscaling factor (x) is defined as: the number of false nodules remaining in the training set (after removing borderline false positive cases) is no more than x times the number of true nodules in the training set. This factor can be adjusted. Decreasing x favors more sensitivity (less specificity). Increasing x favors less sensitivity (more specificity). For false positive reduction, a typical goal is the largest factor (value of x) that maximizes specificity while keeping 100% sensitivity.

Examples were conducted to validate the invention. The first example compared three downscaling methods: random downscaling, systematic downscaling (downscaling factor of 2) and systematic downscaling (downscaling factor of 3).

The dataset was first split into a learning set and a validation set.

|  | Learning set | Validation Set |
| --- | --- | --- |
| True nodules | 67 | 22 |
| False nodules | 483 | 160 |

The data splitting methods used the following patterns.
For random downscaling:

|  | Training | Testing | Total |
| --- | --- | --- | --- |
| True nodules | 50 | 17 | 67 |
| False nodules | 50 | 433 | 483 |

For systematic downscaling (both factor 2 and 3):

|  | Training | Testing | Total |
| --- | --- | --- | --- |
| True nodules | 50 | 17 | 67 |
| False nodules | 360 | 123 | 483 |

For this example, feature subset size 5 through 12 were evaluated, which were previously determined as best feature subset sizes from a feature pool of 23 features. For each size, the executions in the following table were conducted:

| | Downscaling within GA | | |
|---|---|---|---|
| | Random | Factor 2 | Factor 3 |
| Seed 0 | Best feature subset | . . . | Best feature subset |
| Seed 1 | Best feature subset | . . . | Best feature subset |
| Seed 2 | Best feature subset | . . . | Best feature subset |
| Seed 3 | . . . | | . . . |
| Seed 4 | . . . | | . . . |
| Seed 5 | . . . | . . . | . . . |
| Seed 6 | . . . | | . . . |
| Seed 7 | . . . | | . . . |
| Seed 8 | . . . | | . . . |
| Seed 9 | Best feature subset | . . . | Best feature subset |

Besides the data splitting pattern described herein, the following configuration file was used for each GA run. Each GA run consists of 3 independent experiments, with a maximum of 800,000 trials for each of experiment.

```
        experiments = 3
        total trials = 800000
     optimum value = −1.0
        nb of B_genes = 0
        bits per gene = 0
        nb of I_genes = 10
        I_genes range = 10 × 23
             options = LeNwM
random seeds = 98741520 7421398740 123870 521350 99999990
report interval = 100
population size = 50
divergence: max n = 3
n_perf = 2
```

For each of the best feature subset in the above table, a validation was conducted and "sensitivity" (calculated as # of misclassified True Positives) and "specificity" (calculated as % of False Positive reduction) values were obtained and averaged for all 10 seeds. A number of scatter plots (ROC curves) were drawn for comparison (FIGS. 7-14).

One diagram is drawn for each subset size. On the diagram, the X axis represents sensitivity (# of misclassified True Positives), Y axis represents specificity (% of False Positive reduction). There are 3 curves in each diagram, created by validation results on 16 downscaling factors (1.5, 1.6, 1.7 . . . 3.0).

As shown in the diagrams, except for Size 11 and 12, the feature subsets selected by "Systematic downscaling—factor 2" perform better (yield a higher specificity) than feature subsets selected by "Random downscaling" when misclassification of 1-2 true nodules are allowed (it is a reasonable number). This is reflected by the fact that when x has a value between 1 and 2, the Factor2βeatures curve is above the RandomFeatures curve.

This example shows that the feature subset selected by the method is better (greater specificity is obtained) than the previous random data scaling based GA feature subset selection.

It will furthermore be apparent that other and further forms of the invention, and embodiments other than the specific and exemplary embodiments described above, may be devised without departing from the spirit and scope of the appended claims and their equivalents, and therefore it is intended that the scope of this invention encompasses these equivalents and that the description and claims are intended to be exemplary and should not be construed as further limiting.

What is claimed is:

1. A method of improving classification accuracy and reducing false positives in data mining, computer aided-detection, computer-aided diagnosis and artificial intelligence, the method comprising:
    choosing a training set from a set of training cases using systematic data scaling, the training set including one or more training cases for true nodules and one or more training cases for false nodules, the systematic data scaling removing only one or more training cases for false nodules, which is proximate a classification boundary for true and false nodules, from the training set; and,
    creating a classifier based on the training set using a classification method, wherein the systematic data scaling method and the classification method produce the classifier thereby reducing false positives and improving classification accuracy.

2. The method according to claim 1 wherein the classifier is selected from the group consisting of: support vector machines, neural networks, and decision trees.

3. The method according to claim 1, the method further comprising evaluating the classifier produced by the classification method based on the training set using a testing set.

4. The method according to claim 1 wherein choosing further comprises removing from the training set false nodules that form Tomek links with true nodules until a threshold is met.

5. The method according to claim 4 wherein the threshold is determined with respect to a downscaling factor, x, such that the number of false nodules remaining in the training set after systematic data scaling is no more than x times the number of true nodules in the training set.

6. The method according to claim 1 wherein the method further comprises validating the classifier with the set of training cases or a subset thereof.

7. A genetic algorithm that when executed implements the method of claim 1.

8. The genetic algorithm according to claim 7 wherein the genetic algorithm is the CHC algorithm.

9. A method of choosing features from a feature pool, the method comprising: providing each of a first genetic algorithm and a second genetic algorithm according to claim 7, wherein the first genetic algorithm is used to determine the best size of the feature set; and, fixing the feature set size and using the second genetic algorithm to select the features.

10. The method according to claim 9 wherein in providing the first genetic algorithm, the method further comprises analyzing results using at least one of: number of occurrences of chromosomes representing different feature subset sizes and number of average errors.

11. The method according to claim 10, wherein number of average errors is a number of misclassified lung nodules.

12. A non-transitory computer-readable medium which when executed implements the method of claim 1.

13. An article of manufacture which is an imaging device or a false positive reduction device, wherein the device is a computer that is programmed to analyze image data by implementing the method of claim 1.

14. The article of manufacture according to claim 13, wherein the imaging device is selected from the group consisting of: computed tomography (CT), computed axial tomography (CAT), multi-slice computed tomography (MSCT), body section roentgenography, ultrasound, magnetic resonance imaging (MRI), magnetic resonance tomography (MRT), nuclear magnetic resonance (NMR), X-ray, microscopy, fluoroscopy, tomography, and digital imaging.

15. The article of manufacture according to claim 13, wherein the article of manufacture is a lung nodule CAD system.

16. The method of claim 1, wherein the number of the at least one removed training case for false nodules exceeds a threshold, the threshold determined with respect to a downscaling factor, x, wherein the number of false nodules remaining in the training set after systematic data scaling is no more than x times the number of true nodules in the training set.

17. The method of claim 16, wherein the downscaling factor is the largest factor that maximizes specificity while keeping 100% sensitivity.

* * * * *